United States Patent [19]

Goldberg

[11] Patent Number: 4,719,215

[45] Date of Patent: Jan. 12, 1988

[54] QUATERNARY DERIVATIVES OF NOROXYMORPHONE WHICH RELIEVE NAUSEA AND EMESIS

[75] Inventor: Leon I. Goldberg, Chicago, Ill.

[73] Assignee: University of Chicago, Chicago, Ill.

[21] Appl. No.: 837,399

[22] Filed: Mar. 7, 1986

[51] Int. Cl.⁴ ............................................. A61K 31/44
[52] U.S. Cl. ..................................................... 514/282
[58] Field of Search ......................................... 514/282

[56] References Cited

U.S. PATENT DOCUMENTS 4,176,186 11/1979 Goldberg et al. ................. 546/45

Primary Examiner—Stanley J. Friedman
Attorney, Agent, or Firm—Christie, Parker & Hale

[57] ABSTRACT

Quaternary derivatives of noroxymorphone are used to prevent or relieve nausea and emesis associated with the use of narcotic analgesics without interfering with the analgesic activity of the drugs. A particularly preferred compound is methylnaltrexone. The compound is administered in a concentration between 0.25 mg/kg and 1.0 mg/kg prior to or concurrently with the administration of the narcotic analgesic.

11 Claims, No Drawings

QUATERNARY DERIVATIVES OF NOROXYMORPHONE WHICH RELIEVE NAUSEA AND EMESIS

BACKGROUND

The administration of therapeutic doses of morphine and other clinically useful narcotic analgesics is often accompanied by unpleasant side effects on the gastrointestinal system. For instance, morphine and related opiates such as meperidine and methadone may retard intestinal mobility by causing contractions of the small bowel circular smooth muscle.

Morphine and related narcotics may also induce nausea and increased mobility of the gastro-intestinal tract resulting in emesis or vomiting. These side effects are caused by direct stimulation of the chemoreceptor trigger zone for emesis in the area postrema of the medulla. (Goodman and Gilman, *The Pharmacological Basis of Therapeutics*, page 502 [6th ed. 1980], incorporated herein by reference.) Studies have shown that morphine and other narcotics cause emesis in dogs. For example, Wang and Glaviano, JPET 111: 329–334 (1943), incorporated herein by reference, reported that administration of 0.5 mg/kg of morphine intravenously to 12 dogs resulted in emesis in 9 dogs within an average of 2.4 minutes. (Mg/kg refers to milligrams of morphine per kilograms of body weight.) When 1.0 mg/kg of morphine was administered intramuscularly to 13 dogs, 12 of them vomited within an average time of 3.5 minutes.

SUMMARY OF THE INVENTION

U.S. Pat. No. 4,176,186 to myself and others disclosed treatment of intestinal immobility associated with the use of narcotic analgesics through the administration of quaternary derivatives of noroxymorphone. It has now been discovered that the same compounds are also useful for the treatment, both prophylactic and therapeutic, of the nausea and vomiting associated with the administration of these drugs.

According to the invention, therefore, nausea and vomiting by warm-blooded animals receiving morphine and related opiates, meperidine, methadone or the like, may be prevented or relieved by the administration of methylnaltrexone or other quaternary derivatives of noroxymorphone represented by the formula:

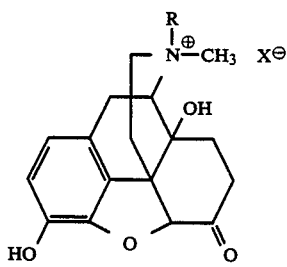

wherein
R is allyl or a related radical such as chloroallyl, cyclopropyl-methyl or propargyl, and
X is the anion of an acid, especially a chloride, bromide, iodide or methylsulfate anion.

These compounds are administered to the animal either prior to or simultaneously with the administration of the narcotic analgesic. They may be administered either enterally or parenterally. There has not been observed any interference with the analgesic activity of the opiates.

As used herein, unless the sense of the usage indicates otherwise, the term "morphine" refers to any narcotic analgesic.

DETAILED DESCRIPTION

This invention relates to the use of quaternary derivatives of noroxymorphone to prevent or relieve nausea and vomiting associated with the administration of morphine to warm-blooded animals. The useful compounds are represented by the formula:

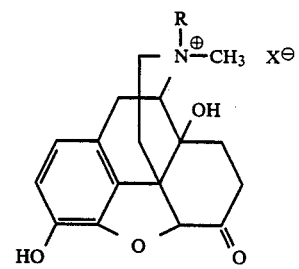

wherein
R is allyl or a related radical such as chloroallyl, cyclopropyl-methyl or propargyl, and
X is the anion of an acid, especially a chloride, bromide, iodide or methylsulfate anion.

The compounds are synthesized as described in U.S. Pat. No. 4,176,186, the disclosure of which is incorporated herein by reference. A particularly preferred noroxymorphone derivative is methylnaltrexone, but other compounds represented by the above formula are also suitable.

Methylnaltrexone or other noroxymorphone derivatives may be administered to the patient either enterally or parenterally. However, a preferred method of administration is by injection. Nausea and emesis may follow after even a single dose of morphine, unlike intestinal immobility which is usually the effect of chronic repeated usage of the drug. Consequently, it is contemplated that the patient will be given an injection of methylnaltrexone prior to surgery or other occasion when morphine is used to treat acute pain.

As illustrated by the following Controls and Examples, our studies show that methylnaltrexone inhibits emesis when administered either together with the morphine or before the morphine is administered. It is thought that methylnaltrexone or other quaternary noroxymorphone derivatives may be administered up to two hours before the administration of morphine, but that period may be variable. In our studies, methylnaltrexone was administered intramuscularly by means of a syringe. It was found effective when administered in the same syringe as morphine and also when administered up to 30 minutes before the administration of morphine. Methylnaltrexone may also be administered enterally or parenterally by other means. It has been found to be effective in the range of about 0.25 mg/kg to about 1.0 mg/kg.

The effect of methylnaltrexone in reversing the emetic effects of morphine is illustrated herein. The unit of mg/kg refers to milligrams of substance administered per kilograms of body weight.

CONTROL 1 AND EXAMPLE 1

One mg/kg of morphine was administered intramuscularly to five dogs. Four dogs vomited. In each instance, vomiting occurred within four minutes. On a different day the same dose of morphine was administered intramuscularly to the same five dogs in the same syringe with 1 mg/kg of methylnaltrexone. None of the dogs vomited.

CONTROL 2 AND EXAMPLE 2

Six dogs were given intramuscular doses of 1 mg/kg of morphine. All six dogs vomited. On an additional day the same dose of morphine was combined with 0.5 mg/kg of methylnaltrexone and administered in the same syringe to the same dogs. None of the dogs vomited.

CONTROL 3 AND EXAMPLE 3

One mg/kg of morphine was administered intramuscularly to three dogs. All three dogs vomited. On an additional day the morphine was combined with 0.25 mg/kg of methylnaltrexone and administered in the same syringe. None of the dogs vomited.

CONTROL 4 AND EXAMPLE 4

Methylnaltrexone was administered to two dogs prior to the administration of 1 mg/kg morphine. In one dog, 0.5 mg/kg of methylnaltrexone was administered intramuscularly 15 minutes before the morphine. No vomiting occurred. In the second dog, the same dose of methylnaltrexone was administered 30 minutes before the administration of morphine. No vomiting occurred.

The administration of methylnaltrexone alone was found to produce no noticeable effects in the animals. Previous studies with larger doses of methylnaltrexone have demonstrated that unlike the non-quaternary naltrexone, methylnaltrexone does not precipitate withdrawal systems in morphine-tolerant dogs. Russell et al., *Eur. J. Pharmacol.* 78: 255–261 (1982), incorporated herein by reference. Methylnaltrexone has not been found to interfere with the analgesic activity of morphine or other narcotics.

What is claimed is:

1. A method for preventing or relieving nausea and emesis associated with the use of narcotic analgesics in warm-blooded animals, which comprises administering to an animal prone towards nausea or emesis on receiving narcotic analgesics, an effective amount of at least one nausea and emesis relieving compound of the formula:

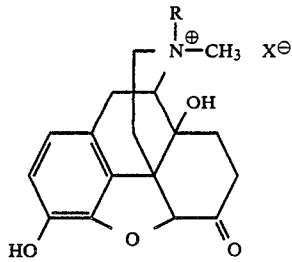

wherein

R is allyl or a related radical such as chloroallyl, cyclopropyl-methyl or propargyl, and X is the anion of an acid, especially a chloride, bromide, iodide or methylsulfate anion, prior to or simultaneously with administration of the narcotic analgesic.

2. A method as claimed in claim 1, where the compound is administered to the animal in an amount between about 0.25 mg/kg and about 1.0 mg/kg.

3. A method as claimed in claim 1, where the compound is administered to the animal enterally.

4. A method as claimed in claim 1, where the compound is administered to the animal parenterally.

5. A method as claimed in claim 4, where the compound is administered to the animal by injection.

6. A method as claimed in claim 1, where the compound is administered to the animal prior to the administration of the narcotic analgesic.

7. A method as claimed in claim 6, where the compound is administered to the animal up to about two hours prior to the administration of the narcotic analgesic.

8. A method as claimed in claim 1, where the compound is administered to the animal concurrently with the administration of the narcotic analgesic.

9. A method as claimed in claim 1, where the compound comprises methylnaltrexone.

10. A method for preventing or relieving nausea and emesis associated with the use of narcotic analgesics in warm-blooded animals, which comprises administering to an animal prone to exhibit nausea or emesis on administration of narcotic analgesics, methylnaltrexone in the amount of between about 0.25 mg/kg and about 1.0 mg/kg simultaneous with or up to about two hours prior to the time of administration of the narcotic analgesic.

11. A method as claimed in claim 10, where the methylnaltrexone is administered to the animal parenterally.

* * * * *

UNITED STATES PATENT AND TRADEMARK OFFICE
CERTIFICATE OF CORRECTION

PATENT NO. : 4,719,215
DATED : January 12, 1988
INVENTOR(S) : Leon I. Goldberg

It is certified that error appears in the above-indentified patent and that said Letters Patent is hereby corrected as shown below:

Column 1, line 5, after the title insert

-- This invention was made with government support under grants GM 22220 and NS12324 awarded by the National Institutes of Health. The government has certain rights in the invention. --

Signed and Sealed this

Eighteenth Day of October, 1994

Attest:

BRUCE LEHMAN

Attesting Officer

Commissioner of Patents and Trademarks